United States Patent [19]
Amory et al.

[11] Patent Number: 5,880,080
[45] Date of Patent: Mar. 9, 1999

[54] USE OF ALKALINE PROTEASES IN INDUSTRIAL TEXTILE LAUNDERING PROCESSES

[75] Inventors: Antoine Amory, Rixensart; André Clippe, Brussels, both of Belgium; Gerhard Konieczny-Janda, Pattensen, Germany

[73] Assignee: Solvay Enzymes GmbH & Co. KG, Nienburg, Germany

[21] Appl. No.: 413,724

[22] Filed: Mar. 31, 1995

[30] Foreign Application Priority Data

Mar. 31, 1994 [DE] Germany ............................ 44 11 223.8

[51] Int. Cl.⁶ .............................. C11D 3/386; B08B 1/00
[52] U.S. Cl. ......................... 510/320; 510/321; 510/392; 510/530; 134/42; 134/25.2
[58] Field of Search ..................... 435/219–225; 252/174.12, DIG. 12, 95; 134/42, 25.2; 510/392, 530, 320, 321

[56] References Cited

U.S. PATENT DOCUMENTS

| | | | |
|---|---|---|---|
| 5,324,653 | 6/1994 | Van Eckelen | 435/221 |
| 5,336,611 | 8/1994 | Van Eckelen | 435/221 |
| 5,352,603 | 10/1994 | Vetter et al. | 435/221 |
| 5,358,865 | 10/1994 | Outtrup et al. | 435/221 |
| 5,385,837 | 1/1995 | Boyer et al. | 435/221 |
| 5,397,705 | 3/1995 | Zukowski et al. | 432/222 |
| 5,453,372 | 9/1995 | Vetter et al. | 435/222 |
| 5,466,594 | 11/1995 | Outtrup et al. | 435/221 |

FOREIGN PATENT DOCUMENTS

| | | |
|---|---|---|
| 415296A | 3/1991 | European Pat. Off. . |
| 503346A | 9/1992 | European Pat. Off. . |
| 610808 | 8/1994 | European Pat. Off. . |
| 42 19 104A | 12/1992 | Germany . |
| 9402618 | 2/1994 | WIPO . |

OTHER PUBLICATIONS

Database WPI; Section Ch, Week 9329; Derwent Publications Ltd., London, GB; Class D13 An 93–231494 XP002027423 & JP 05 153 976 A (Nippon Kagaku Kikai Kogyo KK), Jun. 22, 1993.

Saito, Hiuga and Kin–Ichiro Miura, "Preparation of Transforming Deoxyribonucleic Acid by Phenol Treatment", *Biochimica et Biophysica Acta*, 72 (1963) pp. 619–629.

Chang, Shing and Stanley N. Cohen, "High Frequency Transformation of *Bacillus subtillis* Protoplasts by Plasmid DNA", *Molec. gen Genet.*, 168, pp. 111–115 (1979).

Maniatis T., *Molecular Cloning, A Laboratory Manual*, Cold Spring Harbor Laboratory, Bold Spring Harbor, NY, 1982, pp. iii–x and 86–96.

Kunkel, Thomas A., "Rapid and Efficient Site–Specific Mutagenesis Without Phenotypic Selection", *Proc. Natt. Acaa. SCT. USA*, vol. 82, pp. 488–492, Jan. 1985.

Beaucage, S. L. and M. H. Caruthers, "Deoxynucleoside Phosphoramidites—A New Class of Key Intermediates for Deoxypolynucleotide Synthesis", *Tetrahedron Letters*, vol. 22, No. 20, pp. 1859–1862, 1981.

Kunkel, Thomas A., John D. Roberts and Richard A. Zakour, "Rapid and Efficient Site–Specific Mutagenesis Without Phenotypic Selection", *Methods in Enzymology*, vol. 154, pp. 367–382.

*Primary Examiner*—Paul Lieberman
*Assistant Examiner*—Kery A Fries
*Attorney, Agent, or Firm*—Cooley Godward LLP

[57] ABSTRACT

The use of alkaline bacillus proteases in commercial laundry methods and compositions containing these proteases for commercial laundering are described.

9 Claims, 6 Drawing Sheets

Met Lys Lys Pro Leu Gly Lys Ile Val Ala Ser Thr Ala Leu Leu Ile
-110          -105                    -100
Ser Val Ala Phe Ser Ser Ile Ala Ser Ala Ala Glu Glu Ala Lys
-95              -90              -85                    -80
Glu Lys Tyr Leu Ile Gly Phe Asn Glu Gln Glu Ala Val Ser Glu Phe
                -75                -70                    -65
Val Glu Gln Val Glu Ala Asn Asp Glu Val Ala Ile Leu Ser Glu Glu
            -60              -55                    -50
Glu Glu Val Glu Ile Glu Leu Leu His Glu Phe Glu Thr Ile Pro Val
        -45              -40                -35
Leu Ser Val Glu Leu Ser Pro Glu Asp Val Asp Ala Leu Glu Leu Asp
    -30              -25              -20
Pro Ala Ile Ser Tyr Ile Glu Glu Asp Ala Glu Val Thr Thr Met Ala
-15              -10                -5                       1
Gln Ser Val Pro Trp Gly Ile Ser Arg Val Gln Ala Pro Ala Ala His
             5                  10                 15
Asn Arg Gly Leu Thr Gly Ser Gly Val Lys Val Ala Val Leu Asp Thr
        20              25                  30
Gly Ile Ser Thr His Pro Asp Leu Asn Ile Arg Gly Gly Ala Ser Phe
    35              40              45
Val Pro Gly Glu Pro Ser Thr Gln Asp Gly Asn Gly His Gly Thr His
50              55              60              65
Val Ala Gly Thr Ile Ala Ala Leu Asn Asn Ser Ile Gly Val Leu Gly
            70              75              80
Val Ala Pro Ser Ala Glu Leu Tyr Ala Val Lys Val Leu Gly Ala Ser
        85              90              95

FIG. IA

Gly Ser Gly Ser Val Ser Ser Ile Ala Gln Gly Leu Glu Trp Ala Gly
          100             105             110

Asn Asn Gly Met His Val Ala Asn Leu Ser Leu Gly Ser Pro Ser Pro
    115             120             125

Ser Ala Thr Leu Glu Gln Ala Val Asn Ser Ala Thr Ser Arg Gly Val
130             135             140             145

Leu Val Val Ala Ala Ser Gly Asn Ser Gly Ala Gly Ser Ile Ser Tyr
            150             155             160

Pro Ala Arg Tyr Ala Asn Ala Met Ala Val Gly Ala Thr Asp Gln Asn
        165             170             175

Asn Asn Arg Ala Ser Phe Ser Gln Tyr Gly Ala Gly Leu Asp Ile Val
        180             185             190

Ala Pro Gly Val Asn Val Gln Ser Thr Tyr Pro Gly Ser Thr Tyr Ala
    195             200             205

Ser Leu Asn Gly Thr Ser Met Ala Thr Pro His Val Ala Gly Ala Ala
210             215             220             225

Ala Leu Val Lys Gln Lys Asn Pro Ser Trp Ser Asn Val Gln Ile Arg
            230             235             240

Asn His Leu Lys Asn Thr Ala Thr Ser Leu Gly Ser Thr Asn Leu Tyr
            245             250             255

Gly Ser Gly Leu Val Asn Ala Glu Ala Ala Thr Arg
        260             265

FIG. IB

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 2280 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Bacillus alcalophilus
        ( B ) STRAIN: HA1, DSM 5466

( v i i i ) POSITION IN GENOME:
        ( B ) MAP POSITION: 1192 to 1998 mature peptide
        ( C ) UNITS: bp ( i x ) FEATURE:
        ( A ) NAME/KEY: CDS
        ( B ) LOCATION: 859..1998

( i x ) FEATURE:

( A ) NAME/KEY: mat_eptide
( B ) LOCATION: 1192..1998

( x i ) SEQUENCE DESCRIPTION: SEQ ID NO: 1:

```
CTCGGGAAGC CGATTTGCTA CTGCATGTCG TCGATTATTC AAATGAACGC CATCGCGAAA    60

TGGCAAAGAC GACAAATGAA ACACTCCAGG CAATGGAAAT CGATCGCCCG ATGATTTATG   120

TTTACAACAA AATGGATCAA GTGAAAGACG CGTTTCCTCA AGCGCATGGC ACGAGCTGTT   180

TATATCAGCT AAGGCTAAAC AAGGGCTTGA TTTATTAGCA CAGAAAATAG CAAGCTATGT   240

TTTTCAAGAT TTTGAAAAAC ATCTGTTCAT CATTCCTTAT CGTGACGGGG AGGCGGCTGC   300

TTATTTAAAC AACCATGCCC ATGTCCACAC ACAGCGTGCT GAGGAGGACG GCTGGCATAT   360

CGTTGCCGAT TTGCATGAAC GAGACTTAAA ACGGGTTGAA AGCTACTGTG TTTCAAAAGA   420

ACGATAATGA AAAAGCCAT TTGAATGCTT CTTGTTCAAA TGGCTTTTTG GCGACTATGG   480

TAGACAGATG AACACTTGTT TCGCTGTTTT ACGACAAAGA TCATCTTGCC TGTTACGCGT   540

TTTTTAAATC CGTTTTCGCA CGTTCAATTG TCGCCGAGTC GTACCAGTCG CTGTAAGTGA   600

GAATATGTTT AGAAAGCCGC GTATTTAAGC GCAGTCTTTT TCGTTCTGTA CTGGCTGGTT   660

TGTGGACAGT TTCCATACCC ATCAACCTCC TTTTATTTGT AGCTTTCCCC ACTTGAAACC   720

GTTTAATCA AAAACGAAGT GAGAAGATTC AGTTAACTTA ACGTTAATAT TTGTTTCCCA   780

ATAGGCAAAT CTTTCTAACT TTGATACGTT TAAACTACCA GCTTGGACAA GTTGGTATAA   840

AAATGAGGAG GGAACCGA ATG AAG AAA CCG TTG GGG AAA ATT GTC GCA AGC      891
                    Met Lys Lys Pro Leu Gly Lys Ile Val Ala Ser
                    -111- 110                   -105

ACC GCA CTA CTC ATT TCT GTT GCT TTT AGT TCA TCG ATC GCA TCG GCT      939
Thr Ala Leu Leu Ile Ser Val Ala Phe Ser Ser Ser Ile Ala Ser Ala
-100             -95              -90                       -85

GCT GAA GAA GCA AAA GAA AAA TAT TTA ATT GGC TTT AAT GAG CAG GAA      987
Ala Glu Glu Ala Lys Glu Lys Tyr Leu Ile Gly Phe Asn Glu Gln Glu
             -80               -75                    -70

GCT GTC AGT GAG TTT GTA GAA CAA GTA GAG GCA AAT GAC GAG GTC GCC     1035
Ala Val Ser Glu Phe Val Glu Gln Val Glu Ala Asn Asp Glu Val Ala
         -65                   -60                   -55

ATT CTC TCT GAG GAA GAG GAA GTC GAA ATT GAA TTG CTT CAT GAA TTT     1083
Ile Leu Ser Glu Glu Glu Glu Val Glu Ile Glu Leu Leu His Glu Phe
     -50                   -45                   -40

GAA ACG ATT CCT GTT TTA TCC GTT GAG TTA AGC CCA GAA GAT GTG GAC     1131
Glu Thr Ile Pro Val Leu Ser Val Glu Leu Ser Pro Glu Asp Val Asp
-35                   -30                    -25

GCG CTT GAA CTC GAT CCA GCG ATT TCT TAT ATT GAA GAG GAT GCA GAA     1179
Ala Leu Glu Leu Asp Pro Ala Ile Ser Tyr Ile Glu Glu Asp Ala Glu
-20                   -15                    -10                 -5

GTA ACG ACA ATG GCG CAA TCA GTG CCA TGG GGA ATT AGC CGT GTG CAA     1227
Val Thr Thr Met Ala Gln Ser Val Pro Trp Gly Ile Ser Arg Val Gln
             1                 5                    10

GCC CCA GCT GCC CAT AAC CGT GGA TTG ACA GGT TCT GGT GTA AAA GTT     1275
Ala Pro Ala Ala His Asn Arg Gly Leu Thr Gly Ser Gly Val Lys Val
         15                  20                   25

GCT GTC CTC GAT ACA GGT ATT TCC ACT CAT CCA GAC TTA AAT ATT CGT     1323
Ala Val Leu Asp Thr Gly Ile Ser Thr His Pro Asp Leu Asn Ile Arg
     30                  35                   40

GGT GGC GCT AGC TTT GTA CCA GGG GAA CCA TCC ACT CAA GAT GGG AAT     1371
Gly Gly Ala Ser Phe Val Pro Gly Glu Pro Ser Thr Gln Asp Gly Asn
45                  50                   55                   60

GGG CAT GGC ACG CAT GTG GCC GGG ACG ATT GCT GCT TTA AAC AAT TCG     1419
Gly His Gly Thr His Val Ala Gly Thr Ile Ala Ala Leu Asn Asn Ser
                65                  70                    75
```

```
ATT  GGC  GTT  CTT  GGC  GTA  GCG  CCG  AGC  GCG  GAA  CTA  TAC  GCT  GTT  AAA    1467
Ile  Gly  Val  Leu  Gly  Val  Ala  Pro  Ser  Ala  Glu  Leu  Tyr  Ala  Val  Lys
               80                      85                      90

GTA  TTA  GGG  GCG  AGC  GGT  TCA  GGT  TCG  GTC  AGC  TCG  ATT  GCC  CAA  GGA    1515
Val  Leu  Gly  Ala  Ser  Gly  Ser  Gly  Ser  Val  Ser  Ser  Ile  Ala  Gln  Gly
          95                      100                     105

TTG  GAA  TGG  GCA  GGG  AAC  AAT  GGC  ATG  CAC  GTT  GCT  AAT  TTG  AGT  TTA    1563
Leu  Glu  Trp  Ala  Gly  Asn  Asn  Gly  Met  His  Val  Ala  Asn  Leu  Ser  Leu
     110                      115                     120

GGA  AGC  CCT  TCG  CCA  AGT  GCC  ACA  CTT  GAG  CAA  GCT  GTT  AAT  AGC  GCG    1611
Gly  Ser  Pro  Ser  Pro  Ser  Ala  Thr  Leu  Glu  Gln  Ala  Val  Asn  Ser  Ala
125                      130                     135                          140

ACT  TCT  AGA  GGC  GTT  CTT  GTT  GTA  GCG  GCA  TCT  GGG  AAT  TCA  GGT  GCA    1659
Thr  Ser  Arg  Gly  Val  Leu  Val  Val  Ala  Ala  Ser  Gly  Asn  Ser  Gly  Ala
               145                     150                     155

GGC  TCA  ATC  AGC  TAT  CCG  GCC  CGT  TAT  GCG  AAC  GCA  ATG  GCA  GTC  GGA    1707
Gly  Ser  Ile  Ser  Tyr  Pro  Ala  Arg  Tyr  Ala  Asn  Ala  Met  Ala  Val  Gly
               160                     165                     170

GCT  ACT  GAC  CAA  AAC  AAC  AAC  CGC  GCC  AGC  TTT  TCA  CAG  TAT  GGC  GCA    1755
Ala  Thr  Asp  Gln  Asn  Asn  Asn  Arg  Ala  Ser  Phe  Ser  Gln  Tyr  Gly  Ala
               175                     180                     185

GGG  CTT  GAC  ATT  GTC  GCA  CCA  GGT  GTA  AAC  GTG  CAG  AGC  ACA  TAC  CCA    1803
Gly  Leu  Asp  Ile  Val  Ala  Pro  Gly  Val  Asn  Val  Gln  Ser  Thr  Tyr  Pro
     190                      195                     200

GGT  TCA  ACG  TAT  GCC  AGC  TTA  AAC  GGT  ACA  TCG  ATG  GCT  ACT  CCT  CAT    1851
Gly  Ser  Thr  Tyr  Ala  Ser  Leu  Asn  Gly  Thr  Ser  Met  Ala  Thr  Pro  His
205                      210                     215                          220

GTT  GCA  GGT  GCA  GCA  GCC  CTT  GTT  AAA  CAA  AAG  AAC  CCA  TCT  TGG  TCC    1899
Val  Ala  Gly  Ala  Ala  Ala  Leu  Val  Lys  Gln  Lys  Asn  Pro  Ser  Trp  Ser
                    225                     230                     235

AAT  GTA  CAA  ATC  CGC  AAT  CAT  CTA  AAG  AAT  ACG  GCA  ACG  AGC  TTA  GGA    1947
Asn  Val  Gln  Ile  Arg  Asn  His  Leu  Lys  Asn  Thr  Ala  Thr  Ser  Leu  Gly
               240                     245                     250

AGC  ACG  AAC  TTG  TAT  GGA  AGC  GGA  CTT  GTC  AAT  GCA  GAA  GCG  GCA  ACA    1995
Ser  Thr  Asn  Leu  Tyr  Gly  Ser  Gly  Leu  Val  Asn  Ala  Glu  Ala  Ala  Thr
               255                     260                     265

CGC  TAATCAATAA  AAAAAGCCTG  TGCGGTTAAA  GGGCACAGCG  TTTTTTTGTG                    2048
Arg

TATGAATCGA  AAAAGAGAAC  AGATCGCAGG  TCTCAAAAAT  CGAGCGTAAA  GGGCTGTTTA             2108

AAGCTCTTTA  CGCTCGCAGG  TCTTATCGCT  ATACAATGGA  AAATTCACGT  CTTTTGACTT             2168

TCATGGCATA  TTTATTTAAG  TATTCGTTTG  CTTTTTCGTA  CTCTCCGTTT  TTCTGGTACC             2228

ATTGCGCCAG  CTCAATTGCA  TAGTGGACTG  GTTCTTCTTT  ATTATCAAGC  TT                     2280
```

( 2 ) INFORMATION FOR SEQ ID NO: 2:

( i ) SEQUENCE CHARACTERISTICS:
        ( A ) LENGTH: 380 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 2:

```
Met   Lys   Lys   Pro   Leu   Gly   Lys   Ile   Val   Ala   Ser   Thr   Ala   Leu   Leu   Ile
-111  -110                     -105                     -100

Ser   Val   Ala   Phe   Ser   Ser   Ser   Ile   Ala   Ser   Ala   Ala   Glu   Glu   Ala   Lys
-95                     -90                      -85                           -80

Glu   Lys   Tyr   Leu   Ile   Gly   Phe   Asn   Glu   Gln   Glu   Ala   Val   Ser   Glu   Phe
                        -75                      -70                           -65
```

-continued

```
Val Glu Gln Val Glu Ala Asn Asp Glu Val Ala Ile Leu Ser Glu Glu
        -60              -55                        -50
Glu Glu Val Glu Ile Glu Leu Leu His Glu Phe Glu Thr Ile Pro Val
        -45              -40                   -35
Leu Ser Val Glu Leu Ser Pro Glu Asp Val Asp Ala Leu Glu Leu Asp
    -30              -25              -20
Pro Ala Ile Ser Tyr Ile Glu Glu Asp Ala Glu Val Thr Thr Met Ala
-15              -10                    -5                       1
Gln Ser Val Pro Trp Gly Ile Ser Arg Val Gln Ala Pro Ala Ala His
              5                   10                    15
Asn Arg Gly Leu Thr Gly Ser Gly Val Lys Val Ala Val Leu Asp Thr
          20              25                        30
Gly Ile Ser Thr His Pro Asp Leu Asn Ile Arg Gly Gly Ala Ser Phe
    35              40                    45
Val Pro Gly Glu Pro Ser Thr Gln Asp Gly Asn Gly His Gly Thr His
50                  55                  60                    65
Val Ala Gly Thr Ile Ala Ala Leu Asn Asn Ser Ile Gly Val Leu Gly
              70              75                        80
Val Ala Pro Ser Ala Glu Leu Tyr Ala Val Lys Val Leu Gly Ala Ser
          85              90                        95
Gly Ser Gly Ser Val Ser Ser Ile Ala Gln Gly Leu Glu Trp Ala Gly
        100             105                       110
Asn Asn Gly Met His Val Ala Asn Leu Ser Leu Gly Ser Pro Ser Pro
    115             120                       125
Ser Ala Thr Leu Glu Gln Ala Val Asn Ser Ala Thr Ser Arg Gly Val
130             135                 140                     145
Leu Val Val Ala Ala Ser Gly Asn Ser Gly Ala Gly Ser Ile Ser Tyr
            150                 155                     160
Pro Ala Arg Tyr Ala Asn Ala Met Ala Val Gly Ala Thr Asp Gln Asn
        165                 170                     175
Asn Asn Arg Ala Ser Phe Ser Gln Tyr Gly Ala Gly Leu Asp Ile Val
    180                 185                 190
Ala Pro Gly Val Asn Val Gln Ser Thr Tyr Pro Gly Ser Thr Tyr Ala
    195                 200                 205
Ser Leu Asn Gly Thr Ser Met Ala Thr Pro His Val Ala Gly Ala Ala
210                 215                 220                     225
Ala Leu Val Lys Gln Lys Asn Pro Ser Trp Ser Asn Val Gln Ile Arg
            230                 235                     240
Asn His Leu Lys Asn Thr Ala Thr Ser Leu Gly Ser Thr Asn Leu Tyr
        245                 250                     255
Gly Ser Gly Leu Val Asn Ala Glu Ala Ala Thr Arg
        260                 265
```

USE OF ALKALINE PROTEASES IN INDUSTRIAL TEXTILE LAUNDERING PROCESSES

BACKGROUND OF THE INVENTION

This invention relates to the use of alkaline proteases in commercial laundry methods and to compositions for use in commercial laundry methods which contain alkaline proteases.

The textile detergents used in commercial laundries differ in many ways from the detergents normally used domestically. Commercial laundries employ large washer systems which operate either cyclically in response to a timer or continuously and have a very high laundry throughput. These commercial washer systems use different detergent combinations depending on the type of textile and the degree of soiling with the detergent being dispensed in measured amounts into the washing solution in various washing stages such as wetting, prewashing, clear washing and rinsing. The need to utilize water and energy economically has made it necessary to develop for commercial laundering special partly formulated detergent combinations which can be adjusted optimally for the particular washing stage depending on the type and soiling of the textiles to be washed.

It has long been known to use protease-containing detergent compositions in commercial laundries, for example for cleaning hospital laundry contaminated with blood or protective clothing from meat-processing operations. Because the conditions in commercial laundry methods are more severe than in domestic washing machines, particularly high demands are made of the proteases used therein. In addition to good stability and activity at highly alkaline pH values, proteases to be used in commercial laundry systems should have a temperature stability which is sufficiently high to produce good washing results for the particular laundering cycle at low concentration for the maximum length of time at the high temperatures which prevail in commercial laundry methods. In addition, the alkaline proteases used should have minimum sensitivity to the detergent ingredients customary in commercial laundry methods, such as, for example, surfactants, bleaches or disinfectants. Thus, there has remained a need for alkaline proteases which are suitable for commercial laundry methods.

SUMMARY OF THE INVENTION

It was therefore the object of the present invention to provide a textile laundering method which employs new alkaline proteases particularly suitable for use under the conditions encountered in commercial laundry systems.

Another object of the invention is to provide detergent compositions which comprise new alkaline proteases particularly suitable for use under the conditions encountered in commercial laundry systems.

These and other objects of the invention have been achieved in accordance with the present invention by providing a method of laundering a soiled textile comprising washing the textile in the presence of a detergent formulation comprising at least one conventional detergent ingredient and at least one alkaline protease selected from the group consisting of a) protease secreted by the Bacillus strain DSM 6845, and b) protease secreted by the Bacillus strain DSM 5466 and having an amino-acid sequence which differs from the amino-acid sequence of FIG. 1 by at least one amino-acid replacement selected from the group consisting of Q12R, N42R, N74R, N114R, N115R, Q135R, M216Q, N237P, and T249R.

In accordance with a further aspect of the invention, the objects have also been achieved by providing a detergent composition suitable for commercial laundry methods comprising at least one conventional detergent ingredient and at least one alkaline protease selected from the group consisting of a) alkaline Bacillus protease from Bacillus strain DSM 6845, and b) alkaline Bacillus protease from Bacillus strain DSM 5466 having an amino-acid sequence which differs from the amino-acid sequence of FIG. 1 by at least one amino-acid substitution selected from the group consisting of Q12R, N42R, N74R, N114R, N115R, Q135R, M216Q, N237P and T249R.

It has now been found that the alkaline bacillus proteases described hereinafter can be used with high wash efficiency in commercial laundry methods. The invention therefore relates to the use of alkaline proteases in compositions for commercial laundry methods, wherein at least one alkaline protease selected from the group of alkaline bacillus proteases from a) the Bacillus strain DSM 6845 and/or b) the Bacillus strain DSM 5466 with an amino-acid sequence which differs from the amino-acid sequence of FIG. 1 by at least one of the amino-acid replacements Q12R, N42R, N74R, N114R, N115R, Q135R, M216Q, N237P, T249R is used.

These alkaline bacillus proteases have molecular weights in the range from 26,000 to 28,000 g/mole, measured by SDS polyacrylamide gel electrophoresis comparing with reference proteins of known molecular weight. Their pH optimum is in the range from 8 to 13.0. As used herein, the term "pH optimum" refers to the pH range in which the proteases display maximum proteolytic activity. These alkaline bacillus proteases also exhibit good pH stability.

Alkaline bacillus proteases from the bacillus strain deposited in the Deutsche Sammlung von Mikroorganismen on Dec. 16, 1991 under the number DSM 6845 can be obtained by cultivation of this strain from the culture supernatant.

An alkaline bacillus protease from the bacillus strain deposited in the Deutsche Sammlung von Mikroorganismen on Jul. 28, 1989 under the number DSM No. 5466, which protease has an amino-acid sequence which differs from the amino-acid sequence of FIG. 1 at the indicated positions, can be obtained in a known manner by point mutation in the amino-acid sequence as described, for example, in U.S. Pat. No. 5,352,603, the entire disclosure of which is incorporated herein by reference.

In a preferred variant, an alkaline bacillus protease from the strain DSM 6845 which has the following properties:

(1) activity: breakdown of proteins and peptides;

(2) pH optimum: approximately at pH values of 8.5–13.0, (3) pH stability: the protease proves to be completely stable at pH values of 9.5–11.0, where "completely stable" means a remaining activity of at least 90%;

(4) temperature optimum: about 64° C.;

(5) temperature stability: the activity of the protease is not significantly impaired by incubation of the protease at temperatures up to 30° C. for 15 minutes; the remaining activity of the protease after incubation at 40° C. for 15 minutes is at least 75%, is used.

The foregoing statement that the activity of the protease is not significantly impaired by incubation at temperatures up to 30° C. for 15 minutes is understood to mean that in comparison to the original activity of the protease, it retains a residual proteolytic activity of at least 92% after the incubation.

In another preferred variant, an alkaline bacillus protease from the strain DSM 5466 is used which has an amino-acid sequence which differs from the amino-acid sequence of FIG. 1 by at least one of the amino-acid replacements Q12R, N42R, N114R, N115R, Q135R, M216Q, N237P or T249R, preferably by the amino-acid substitutions N42R/N114R/N115R or N42R/N114R/M216Q. The numerical values in these notations refer to the positions in the amino-acid sequence. The amino acids are identified by the one-letter codes, with the original amino acid preceding the position indicator and the inserted amino acid following the position indicator. These amino-acid replacements can be obtained in a known manner by point mutation in the amino-acid sequence as described, for example, in U.S. Pat. No. 5,352,603.

These alkaline bacillus proteases show unusually good washing performance under the conditions customary in commercial laundries, such as high pH values, short washing times and high washing temperatures. Commercial laundry processes are typically carried out at temperatures between 30° C. and 70° C. and at pH values above 11.0, particularly at pH values between 11.0 and 13.0. These proteases also show a surprisingly high resistance to inactivation by the detergent constituents customary in commercial laundry methods. Thus, these alkaline bacillus proteases can advantageously be used according to the invention in commercial large-capacity drum-type washing machines or countercurrent batch washing machines operating cyclically in response to a timer or continuously. Moreover, it is particularly advantageous or the alkaline bacillus proteases to be added to the washing solution in the prewash step in so-called multi-solution methods, for example dual wash cycles composed of prewash step and clear-wash step. The prewashing can moreover be carried out under the conditions customary in commercial laundry methods, for example at temperatures from 30° to 70° C. in a known manner with the detergent ingredients customarily used in this laundering cycle. Where the contaminants have a high protein content, for example heavily blood-spotted laundry from hospitals, large kitchens or meat-processing operations, the proteases of the invention optionally can be used very successfully in a prerinse step, which precedes the prewash step, with clear cold or recycled hot water and the other detergent ingredients customary for this purpose. It is, of course, also possible for these alkaline bacillus proteases to be used according to the invention in all other commercial laundry methods, for example in commercial laundry methods suited to particular types of textiles and soils, such as, for example, in the disinfecting laundering of textiles from the hospital sector.

The invention furthermore includes within its scope compositions for commercial laundry methods which contain at least one alkaline bacillus protease from
 a) the Bacillus strain DSM 6845 and/or
 b) the Bacillus strain DSM 5466 with an amino-acid sequence which differs from the amino-acid sequence of FIG. 1 by at least one of the amino-acid substitutions Q12R, N42R, N74R, N114R, N115R, Q135R, M216Q, N237P or T249R.

The compositions according to the invention preferably contain an alkaline bacillus protease from the Bacillus strain DSM 6845 which is characterized by the properties described above.

In a variant which is likewise preferred, the compositions according to the invention contain an alkaline bacillus protease from the strain DSM 5466 with an amino-acid sequence which differs from the amino-acid sequence of FIG. 1 by at least one of the amino-acid substitutions Q12R, N42R, N114R, N115R, Q135R, M216Q, N237P, T249R, in particular by the amino-acid replacements N42R/N114R/N115R or N42R/N114R/M216Q.

The alkaline bacillus proteases which should preferably be used in the compositions according to the invention are those which have an enzyme activity of 50,000 to 1,000,000 DU per gram of enzyme preparation. As used herein, the term "DU" refers to the enzymatic activity in Delft units, where 1000 DU correspond to the proteolytic activity which, with a volume of 1 ml of a 2% (W/W) strength enzyme solution, gives after breakdown of casein an extinction difference (1 cm path length; 275 nm; determination with blank sample test as reference) of 0.4000. Moreover, these alkaline bacillus proteases can be used in the formulations customary for commercial laundry methods either individually or in combination with one another, and optionally also in combination with conventional detergent proteases or other detergent enzymes customary in commercial laundry formulations, such as, for example, amylases, lipases, pectinases, nucleases, oxidoreductases etc. In the detergent formulations according to the invention, the content of these bacillus proteases should preferably be 0.1 to 5% by weight, in particular 0.2 to 2.0% by weight, with respect to the dry matter of the overall composition.

The compositions according to the invention may take the form of complete heavy duty detergents, individual detergents, and/or prewash or prerinse compositions, which are conventional for commercial laundry methods. It is moreover possible, depending on the type of detergent, for all the detergent ingredients customary in the state of the art, such as surfactants, bleaches, builders, laundry aids, optical brighteners and other customary components such as, for example, sodium carbonate, metasilicate, orthophosphate or sodium triphosphate, to be present in customary amounts. Other examples of possible detergent ingredients include boosters, enzyme stabilizers, soil suspending agents and/or compatibilizers, complexing and chelating agents, foam regulators and additives such as corrosion inhibitors, anti-static agents, perfumes, disinfectants, bleach activators, per-acid bleach precursors and anti-greying agents.

The detergent compositions according to the invention are preferably prewash compositions as are used in commercial laundry methods in the temperature range from 30° to 70° C. in so-called multi-solution methods, for example in dual wash cycles comprising a prewash step and a clear-wash step. In addition to these alkaline bacillus proteases, the prewash compositions according to the invention can contain all ingredients customary for this purpose in the commercial sector, such as, for example, nonionic surfactants, phosphates, carbonates, silicates, and if desired perborates and/or bleach activators, anti-greying agents, polycarboxylates, optical brighteners and, optionally further buffer substances and auxiliaries. It is also possible to use commercially obtainable detergent formulations to which the alkaline bacillus proteases of the invention have been added in the stated amounts. If desired, these commercially obtainable formulations may also contain oxygen-based bleaches. Examples of suitable commercially available detergent formulations for the commercial sector include the products sold under the designations TEN-COLOR™ or TENAX CONC.™.

The detergent compositions according to the invention can be formulated in a known manner in powder form, for example in the form of granules, prills or pellets, and if desired also provided with surface coatings. Because of their good stability, the bacillus proteases of the invention can also be used in liquid formulations.

Under the conditions customary in commercial laundry methods, such as highly alkaline pH values, for example pH values above 11.0, and high washing temperatures of up to 70° C., the alkaline bacillus proteases of the invention exhibit surprisingly good washing properties. This is all the more surprising since, in comparison to conventional household washing machines, the countercurrent laundry systems used in commercial laundries often operate completely continuously, which usually means that only relatively short washing times are available. Besides high temperature resistance, the alkaline bacillus proteases of the present invention additionally exhibit high enzyme stability in the presence of the customary ingredients of commercial detergents. When used in accordance with the invention, these alkali bacillus proteases are also stable with respect to the bleaches customarily used in the commercial sector, for example, in commercial disinfecting detergents for the hospital sector, in particular with respect to oxygen bleach concentrates, for example based on perborate or hydrogen peroxide.

The following Examples are intended to illustrate the invention in further detail without restricting its scope.

BRIEF DESCRIPTION OF THE DRAWINGS

The invention will be described in further detail hereinafter with reference to the accompanying drawings in which:

FIGS. 1A and 1B are a listing of the amino-acid sequence (SEQ ID NO1) of the alkaline protease from *Bacillus alcalophilus* HA1 (DSM 5466).

EXAMPLES

Figure 2:
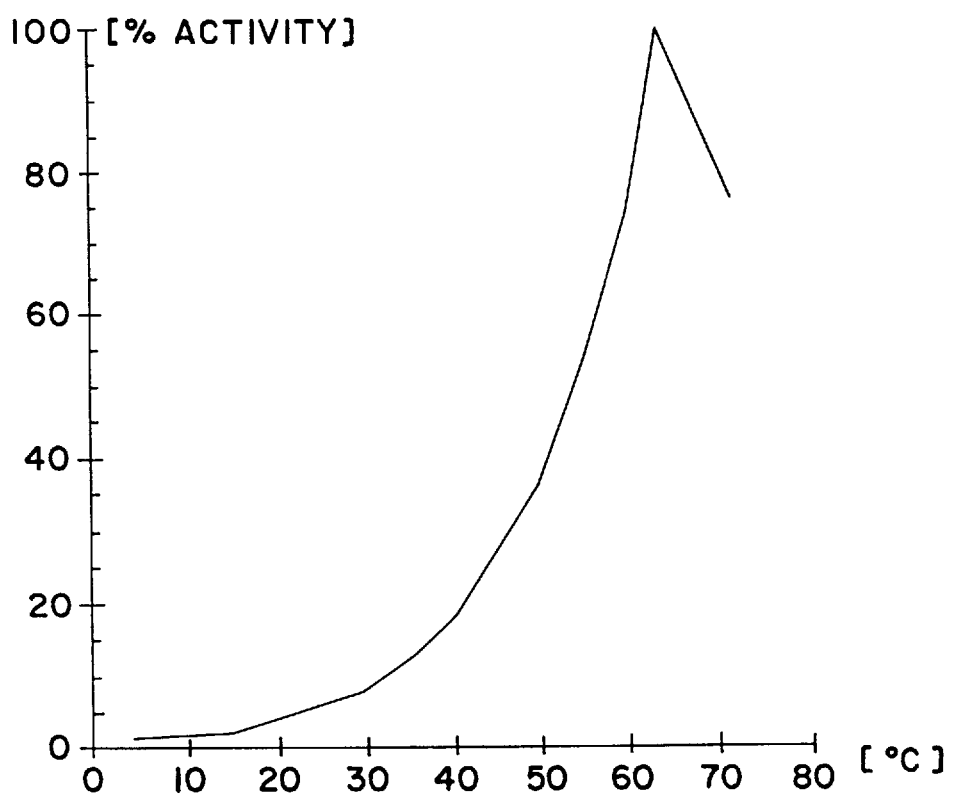
FIG. 2 is graph of the temperature optimum of the protease from Bacillus sp. MF12 (DSM 6845).

The sequencing of the amino-acid sequence, shown in FIG. 1, of the alkaline protease from *Bacillus alcalophilus* HA1 (DSM 5466) via determination of the corresponding nucleotide sequence is described in Examples 1 to 4 in U.S. Pat. No. 5,352,603, the disclosure of which is incorporated herein by reference.

The bacterial strain named Bacillus sp. MF12 strain was deposited at the Deutsche Sammlung von Mikroorganismen (DSM) on Dec. 16, 1991 under the number DSM 6845. The *Bacillus alcalophilus* strain named *Bacillus alcalophilus* HA1 was deposited at the Deutsche Sammlung von Mikroorganismen (DSM) on Jul. 28, 1989 under the number DSM 5466.

Example 1

Preparation of Alkaline Proteases Modified by Mutations in the Amino-Acid Sequence.

The preparation of alkaline proteases which differ from the amino-acid sequence shown in FIG. 1, of the alkaline protease from *Bacillus alcalophilus* HA1 (DSM 5466) by at least one of the amino-acid substitutions Q12R, N42R, N74R, N114R, N115R, Q135R, M216Q, N237P or T249R was carried out in a known manner by directed mutagenesis in partial DNA sequences of the corresponding protease gene. The numerical values in this notation system refer to the corresponding amino-acid position in the amino-acid sequence shown in FIG. 1, with the position indicator being preceded by the one letter code for the original amino acid and followed by the one letter code for the inserted amino acid. The method of directed mutagenesis for the aforementioned mutations is described in detail in Examples 5 to 18 of U.S. Pat. No. 5,352,603. With regard to the amino-acid replacements in positions 42, 114, 216 and 249, additional reference may also be made to published German Patent Application No. DE 4,304,161 [=CA 2,115,465 and U.S. Ser. No. 08/195,721, the disclosure of which is incorporated by reference].

In principle, the method comprised the following known method steps: Chromosomal DNA was isolated from the natural isolate *Bacillus alcalophilus* HA1 (DSM 5466) by the method of Saito et al. [*Biochim. Biophys. Acta* 72:619–629 (1963)] and was partially hydrolyzed with the restriction endonuclease Sau3A. The restriction fragments were fractionated by electrophoresis, and the fragments with a size of 3 to 8 kilobases (kb) were isolated. The isolated and size-selected DNA fragments from *Bacillus alcalophilus* HA1 were recombined in vitro in a known manner with vector DNA of the known plasmid pUB 110. Protoplasts of the strain *Bacillus subtilis* BD224 (Bacillus Genetic Stock Center 1A46) were transformed with the resulting in vitro recombinant DNA by the method described by S. Chang and N. Cohen [*Mol. Gen. Genet.* 168:111–115 (1979)]. The transformants were selected on plates with neomycin. The plasmid DNA was isolated from a clone as described in Maniatis et al. [*Molecular Cloning, A Laboratory Manual*, Cold Spring Harbor Laboratory (1982)]. The fragment, contained in this plasmid, from the *B. alcalophilus* DNA had a size of 4.1 kb and contained the complete DNA sequence for the highly alkaline protease from *Bacillus alcalophilus* HA1 (DSM 5466) (compare Examples 1 and 2 of U.S. Pat. No. 5,352,603).

The plasmid containing the complete DNA sequence for the highly alkaline protease from *Bacillus alcalophilus* HA1 (DSM 5466) was restricted with AvaI. The protruding ends were filled in in a known manner (see Maniatis et al., p. 114) to give the DNA double strand. After subsequent restriction of this DNA with XbaI, the N-terminal fragment comprising 1618 base pairs (bp) was isolated and cloned into the vector pBS in a known manner. The resulting vector contained the N-terminal end of the DNA coding for the amino-acid sequence depicted in FIG. 1 (compare Example 5 of U.S. Pat. No. 5,352,603).

A vector which contained a DNA fragment comprising 658 bp and coding for the C-terminal end of the corresponding protease was produced in an analogous manner. For this purpose, the plasmid containing the complete DNA sequence was cut with the restriction endonucleases XbaI and Asp718 and cloned into the appropriate cleavage site of the known vector pBS (compare Example 7 of U.S. Pat. No. 5,352,603).

The directed mutations were carried out in the DNA partial sequences containing the C-terminal or the N-terminal end by the primer extension technique described by Kunkel, T. A. [*Proc. Natl. Acad. Sci. USA* 82:488–492 (1985)]. For this purpose, the appropriate vectors were first converted in a known manner into their uracilated single-stranded analogues by cultivating *E. coli* CJ236 bacteria which had been transformed with one of the two vectors and which were additionally infected with the helper phage M13

K07 (purchased from Bio-Rad Laboratories, Richmond, Calif.). The bacterium *E. coli* CJ236 is a known uracil N-glycosylase-deficient mutant which on replication of the vectors incorporates the nucleotide uracil in place of thymidine into the DNA sequence of the vector. Uracilated vectors can be advantageously used in a known manner for in vitro reactions of directed mutagenesis because, after termination of the reactions, the uracil-containing DNA single strand which was used as template to generate mutated DNA strands can be eliminated by treatment with uracil N-glycosylase. The use of these helper phages was necessary for the synthesis of the coat proteins for the resulting uracilated single-stranded vector DNA. Coated uracilated single-stranded vector DNA was secreted from the transformed host organism *E. coli* CJ236 and subsequently isolated from the culture medium.

The isolated, uracilated DNA single strand vectors of the respective C-terminal or N-terminal end were hybridized with synthetic oligonucleotides which contained a mutation site and were simultaneously used as primers for the subsequent completion to the complete DNA double strand with mutation. The synthetic oligonucleotides used in this case were prepared in a known manner by the method of Beaucage, S. L. and Caruthers, M. H. [*Tetrahedron Letters* 22:1859–62 (1981)]. The second DNA strand was synthesized in a known manner using T4 DNA polymerase and subsequent ligation with T4 DNA ligase [Kunkel et al., *Methods in Enzymol.* 154:367–82 (1987)]. The resulting double-stranded vector DNA was transformed into *E. coli* MC 1061, and the mutated vectors were identified by checking the appropriate unique restriction endonuclease recognition sites which had been introduced or deleted with the synthetic oligonucleotides.

To produce, for example, two mutations either in the N-terminal or in the C-terminal part of the protease DNA, the first mutation was produced as described above and then the method was repeated in an analogous manner using another synthetic oligonucleotide to introduce a second mutation.

Expression vectors with mutations in the C-terminal part or N-terminal part of the protease DNA sequence were prepared by cutting the DNA sequences obtained by the directed mutagenesis with restriction endonucleases and ligating them to vector DNA which contained the corresponding other terminal part of the DNA sequence and all the elements necessary for expression. The resulting vectors represented complete expression vectors with a suitable reading frame for expressing the appropriately mutated mutase. The preparation of the expression vectors is described in detail in Example 16 of U.S. Pat. No. 5,352,603. Expression vectors were prepared for the following mutations:

DSM 5466 Mut. N114R/M216Q
DSM 5466 Mut. N115R/Q135R
DSM 5466 Mut. N42R/N114R/M216Q
DSM 5466 Mut. N42R/N114Q/N115Q
DSM 5466 Mut. N114R/N237P
DSM 5466 Mut. N42R/N114R
DSM 5466 Mut. Q12R/N42R/N114R
DSM 5466 Mut. N114R/N237P/T249R
DSM 5466 Mut. Q12R/N42R/N114R

The mutated highly alkaline proteases were obtained by transforming *B. subtilis* BD 224 with a respective one of the aforementioned expression vectors in a known manner. The mutated highly alkaline proteases were isolated by known methods from the culture supernatants from these transformed strains. Detailed information on the isolation of the mutated proteases is found in Examples 16 and 18 of U.S. Pat. No. 5,352,603.

The alkaline proteases obtained by mutating the amino acid sequence of the protease from *Bacillus alcalophilus* HA1 (DSM 5466) were used in washing tests described in Example 3.

Example 2

Isolation of an Alkaline Protease from Bacillus sp. MF12 DSM 6845.

50 ml of Luria broth pH 9.5 (10 g of yeast extract, 5 g of Tryptone, 5 g of NaCl and 50 ml of carbonate buffer ad 1000 ml of double-distilled water) in a 500 ml Erlenmeyer flask with 3 baffles were inoculated with a single colony of the strain Bacillus sp. MF12 DSM 6845 (grown on P8A agar plates) and incubated at 37° C. and 240 rpm for 16 hours. 50 ml of main culture medium (soya 2%; starch 5%; corn steep liquor 1%, carbonate buffer 50 ml ($Na_2CO_3$ 4.2%)) in a 500 ml Erlenmeyer flask with 3 baffles were inoculated with 2.5 ml of this culture and incubated at 37° C. and 240 rpm for 48 hours.

The activity of the protease was determined in Delft units (DU). 1000 DU is the proteolytic activity which, with a volume of 1 ml of a 2% (w/w) strength enzyme solution, gives after breakdown of casein an extinction difference (1 cm path length; 275 nm; determination with blank sample test as reference) of 0.4000.

The proteolytic activity in the culture supernatant obtained by centrifugation at 27,000×g for 15 minutes was 5000 DU/ml after 48 hours.

The temperature optimum of the proteases contained in the culture supernatants was determined in the range from 40° to 72° C. The results are shown in Table 1 and in FIG. 2.

The temperature optimum of the protease from Bacillus sp. MF12 DSM 6845 is at 64° C.

TABLE 1

Temperature optimum of the alkaline protease from Bacillus sp. MF12 DSM 6845

% Activity as a function of the temperature in °C.

| 40° C. | 50° C. | 55° C. | 60° C. | 64° C. | 72° C. |
|--------|--------|--------|--------|--------|--------|
| 18%    | 37%    | 53%    | 74%    | 100%   | 76%    |

Figure 3:
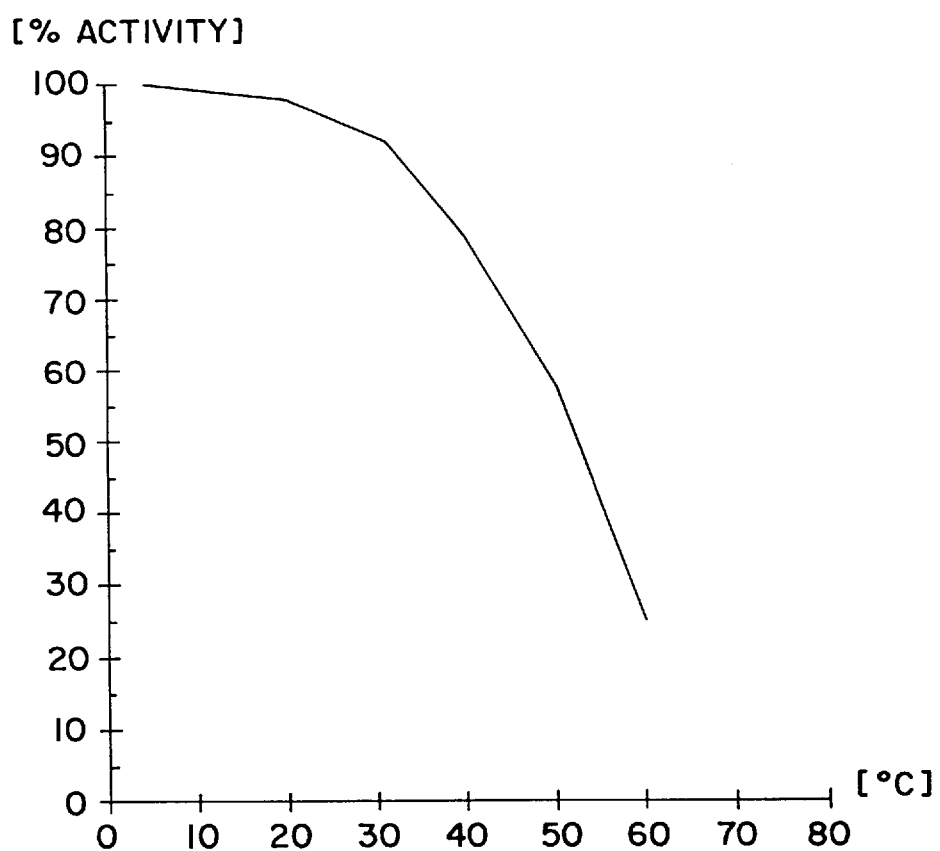
FIG. 3 is a graph showing the temperature stability of the protease from Bacillus sp. MF12 (DSM 6845).

To determine the temperature stability, the protease-containing supernatant was incubated at various temperatures for 15 minutes and subsequently the remaining activity was determined. The results are shown in Table 2 and in FIG. 3.

The protease from Bacillus sp. MF12 DSM 6845 is stable up to 31° C. (remaining activity>90%) and still shows a remaining activity of 58% after incubation at 50° C. for 15 minutes.

TABLE 2

| Temperature [°C.] | Remaining proteolytic activity in % after incubation at various temperatures for 15 minutes |
|---|---|
| 4  | 100 |
| 20 | 98  |
| 31 | 92  |

TABLE 2-continued

| Temperature [°C.] | Remaining proteolytic activity in % after incubation at various temperatures for 15 minutes |
|---|---|
| 40 | 79 |
| 50 | 58 |
| 60 | 25 |

Figure 4:
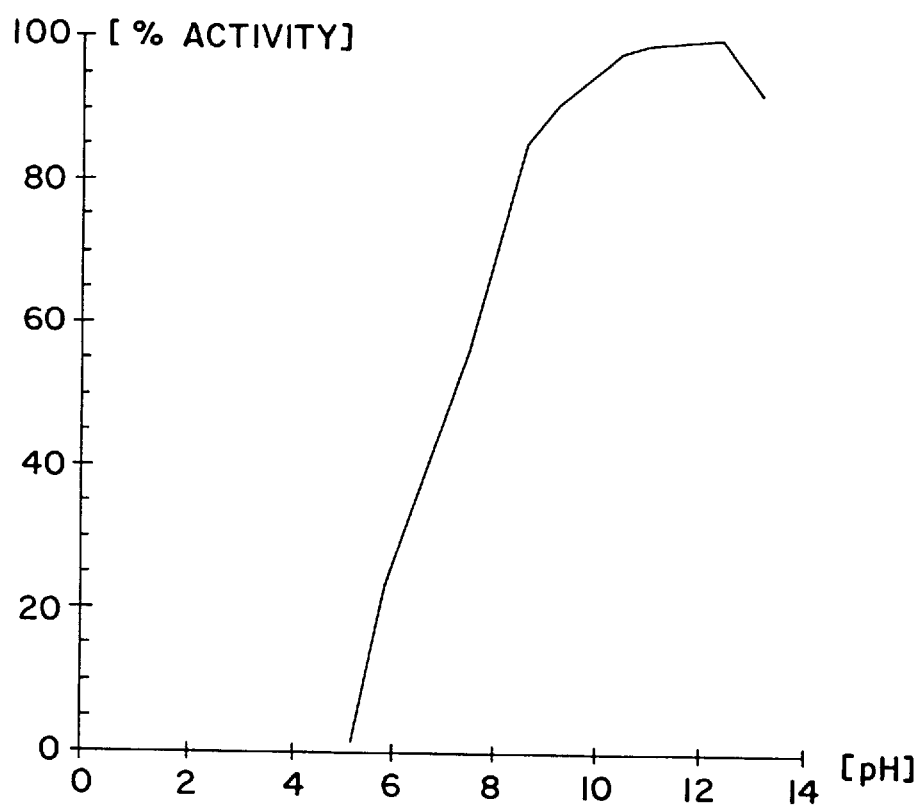
FIG. 4 is a graph showing the pH optimum of the protease from Bacillus sp. MF12 (DSM 6845).

To determine the pH optimum of the protease from Bacillus sp. MF12 DSM 6845, the activity was determined at various pH values. The pH was adjusted with phosphate buffer (0.1M) in the pH range 5.0 to 7.0, with tris-HCl buffer (0.1M) in the pH range 7.0 to 9.0, and with glycine-NaOH buffer (0.1M) in the pH range 9.0 to 13.0. The activity values determined are shown in FIG. 4.

The pH optimum of the alkaline protease from Bacillus sp. MF12 DSM 6845 is around pH 12. The activity is still greater than 90% at pH 13.

Figure 5:
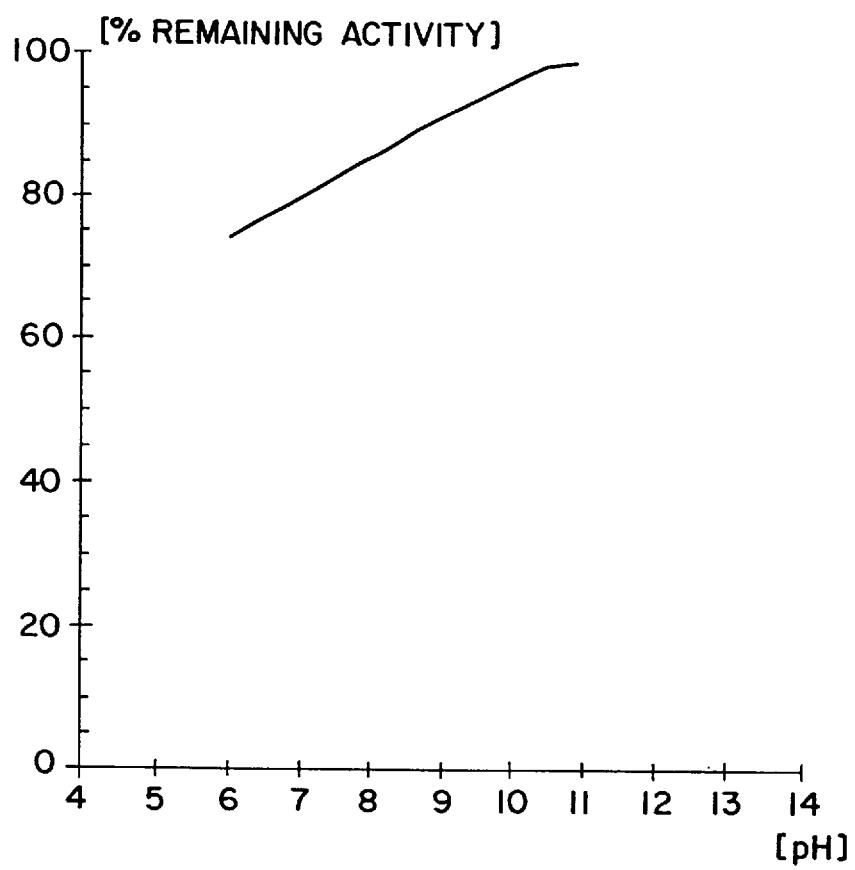
FIG. 5 is a graph showing the pH stability of the protease from Bacillus sp. MF12 (DSM 6845).

To investigate the pH stability, the protease from Bacillus sp. MF12 DSM 6845 was incubated in buffers having various pH values at 4° C. for 24 hours. The remaining activity of the proteases was then determined. Phosphate buffer (0.1M) was used for the pH range from 5 to 7.1, tris-HCl buffer (tris(hydroxymethyl)aminomethane buffer) (0.1M) was used for the pH range from 7.5 to 9, and glycine/sodium hydroxide buffer (0.1M) was used for the pH range from 9 to 12.1. The result is shown in FIG. 5.

The alkaline protease from Bacillus sp. MF12 DSM 6845 still has a minimum of 70% activity remaining after the 24-hour incubation in the entire pH range, and is completely stable around pH 11.

Example 3

Washing Tests under Conditions Customary in Commercial Laundry Methods.

Washing tests were carried out with soiled test fabric under conditions customary in commercial methods. The test fabrics used were a polyester/cotton blend fabric purchased from the eidgenössische Materialprüfungsanstalt, St. Gallen, Switzerland (EMPA117) soiled with blood, milk and India ink, a polyester/cotton blend fabric of our own manufacture (EY-PC) soiled with egg yolk and India ink, and a polyester/cotton blend fabric of our own manufacture (M-PC) soiled with milk and India ink. Washing was carried out in Zelltex Polycolor laboratory washing machines using as basic detergent formulations the prewash compositions which are customary in the commercial sector and are obtainable under the proprietary names TEN COLOR™ and TENAX CONC.™ (manufactured by J. P. Haas, Steinau, Germany). Washing was carried out in the temperature range from 15° C. to 60° C. for 45 minutes (temperature increased from 15° C. to 60° C. at a rate of 2° C./min. and then maintained at 60° C. for 22.5 min) or in the temperature range from 15° C. to 65° C. for 25 minutes (temperature increased from 15° C. to 65° C. at a rate of 5° C./min. and then maintained at 65° C. for 15 min). The water hardness was 15° German hardness; the enzyme concentration was 0.71 mg of pure protease per liter of washing solution. The test fabric was exposed to the enzyme-containing detergent solution in a rotating sample vessel chamber which was controlled by a water bath in accordance with the temperature program. After the washing process the test fabric was rinsed twice with deionized water and then ironed.

The washing performance of the proteases was determined by measuring the reflectance of the washed test fabric using a reflectance photometer. The reflectance of the test fabric washed only with the basic detergent formulation was likewise measured. The difference between these two reflectance values is called the ΔR value and is a measure of the washing performance of the particular protease. For comparison with proteases heretofore used in detergent formulations for commercial laundry systems, all the washing tests were likewise carried out under identical conditions with the protease which is commercially available under the proprietary name Opticlean™.

Table 3 shows the washing performances of the proteases used according to the invention with a bleach-free detergent formulation for commercial laundry methods commercially available under the proprietary name TENAX CONC.™

TABLE 3

Washing performance of proteases used according to the invention on test fabric EMPA117 using a bleach-free prewash formulation for commercial laundry methods.

Washing conditions 15–60° C. (2° C./min, kept at 60° C. for 22.5 min), wash time 45 min, pH 11.5
Enzyme dosage 0.71 mg/l

| Protease | EMPA117 ΔR | EY-PC with egg yolk ΔR | M-PC with milk ΔR | Total ΔR | |
|---|---|---|---|---|---|
| Opticlean ™ | 13.43 | 3.41 | 4.21 | 21.05 | 100% |
| DSM5466 Mut. N114R/M216Q | 12.07 | 6.15 | 4.97 | 23.19 | 110% |
| DSM5466 Mut. N115R/Q13SR | 14.12 | 3.38 | 5.77 | 23.27 | 111% |
| DSM5466 Mut. N42R/N114R/M216Q | 13.14 | 6.81 | 7.66 | 27.61 | 131% |
| DSM5466 Mut. N42R/N114R/N115R | 13.92 | 8.01 | 6.22 | 28.15 | 134% |
| MF12 DSM 6845 | 17.31 | 9.32 | 5.27 | 31.90 | 152% |

Table 4 shows the washing performance of the proteases used according to the invention with a detergent formulation for commercial laundry methods commercially available under the proprietary name TEN-COLOR™ which contains oxygen-based bleach (perborate).

TABLE 4

Washing performance of proteases according to the invention used on test fabric EMPA117 using a detergent formulation for commercial textile laundry methods with bleach.

Washing conditions 15–60° C. (2° C./min, kept at 60° C. for 22.5 min), wash time 45 min, pH 11.5
Enzyme dosage 0.71 mg/l

| Protease | EMPA117 ΔR | EY-PC with egg yolk ΔR | Total ΔR | |
|---|---|---|---|---|
| Opticlean ™ | 12.35 | 5.09 | 17.44 | 100% |
| DSM 5466 Mut. N114R/N237P | 12.92 | 5.55 | 18.47 | 106% |
| DSM 5466 Mut. N42R/N114R | 13.49 | 5.12 | 18.61 | 107% |
| DSM 5466 Mut. Q12R/N42R/N114R | 13.66 | 5.04 | 18.70 | 107% |
| DSM 5466 Mut. N114R/N237P/T249R | 14.32 | 4.69 | 19.01 | 109% |
| DSM 5466 Mut. N42R/N114R/M216Q | 11.66 | 7.40 | 19.06 | 109% |
| DSM 5466 Mut. | 18.44 | 6.7 | 25.14 | 144% |

TABLE 4-continued

Washing performance of proteases according to the invention used on test fabric EMPA117 using a detergent formulation for commercial textile laundry methods with bleach.

| | | | | |
|---|---|---|---|---|
| N42R/N114R/N115R MF12 DSM 6845 | 13.16 | 7.72 | 20.88 | 120% |

The high reflectance values of the proteases used according to the invention demonstrate their high washing performance on protein-soiled fabric under the conditions customary in commercial laundry methods (high alkaline pH values, kept at high temperatures for long times).

In addition to the tests of washing efficiency on the test fabric EMPA117, washing tests were also carried out with the test fabric EY-PC soiled with egg yolk/India ink and with the test fabric M-PC soiled with milk/India ink. The washing test conditions also were made more severe in that the heating rate was increased to 5° C./min and the wash solution was then maintained at a temperature of 65° C. for 15 min. The bleach-containing detergent formulation TEN-COLOR™ for commercial laundry methods was likewise used in these washing tests. Table 5 shows the results obtained in these tests.

TABLE 5

Washing performance of proteases according to the invention used on test fabrics EMPA117, EY-PC and M-PC with a bleach-containing commercial laundry detergent formulation.

| | |
|---|---|
| Washing conditions | 15–65° C. (5° C./min, kept at 65° C. for 15 min), washing time 25 min |
| Enzyme dosage | 0.71 mg/l |

TABLE 5-continued

Washing performance of proteases according to the invention used on test fabrics EMPA117, EY-PC and M-PC with a bleach-containing commercial laundry detergent formulation.

| Protease | EMPA117 ΔR | EY-PC ΔR | M-PC ΔR | Total ΔR | |
|---|---|---|---|---|---|
| Opticlean ™ | 9.10 | 3.46 | 1.82 | 14.38 | 100% |
| DSM 5466 Mut. N42R/N114R/N115R | 14.84 | 5.13 | 2.85 | 22.82 | 159% |
| DSM 5466 Mut. N42R/N114R/M216Q | 9.10 | 6.48 | 4.56 | 20.14 | 140% |
| MF12 DSM 6845 | 9.51 | 7.33 | 3.45 | 20.29 | 141% |

It can be seen from Tables 3 through 5 that the proteases used according to the invention exhibit very good washing performance on various types of fabric soiled with different protein contaminants. Moreover, there is virtually no detectable impairment of the enzyme stability by the highly alkaline medium of the washing solution, by the high washing temperature and/or by the bleach. Furthermore, exceptionally good washing performance is obtained with a short washing time of only 25 min. These results show the particularly high suitability of the proteases of the present invention for use in commercial laundry methods.

The foregoing description and examples have been set forth merely to illustrate the invention and are not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A method of laundering a soiled textile comprising washing said textile at temperatures between 30° C. and 70° C. and at pH values above 11.0 in the presence of a detergent formulation comprising (a) a protease secreted from the Bacillus strain DSM 5466 and having an amino-acid sequence which differs from the amino-acid sequence of SEQ ID NO: 1 by at least one amino acid substitution selected from the group consisting of Q12R and N74R and (b) at least one other detergent ingredient.

2. A method according to claim 1, wherein the protease has an amino-acid sequence which further differs from the amino-acid sequence of SEQ ID NO:1 by at least one additional amino-acid replacement selected from the group consisting of N42R, N114R, N115R, Q135R, M216Q, N237P, and T249R.

3. A method according to claim 2, wherein the protease has an amino acid sequence which differs from the amino-acid sequence of SEQ ID NO:1 by the amino-acid replacements Q12R, N42R and N114R.

4. A detergent composition suitable for commercial laundry methods comprising (a) an alkaline Bacillus protease from Bacillus strain 5466 having an amino acid sequence which differs from the amino acid sequence of ID NO: 1 by at least one amino acid substitution selected from the group consisting of Q12R and N74R and (b) at least one other detergent ingredient.

5. A composition according to claim 4, wherein said at least one protease has an activity of from 50,000 to 1,000,000 DU per gram.

6. A composition according to claim 5, comprising from 0.1 to 5.0 wt-% of said at least one protease.

7. A composition according to claim 4, further comprising an oxygen bleach.

8. A composition according to claim 4, wherein the protease has an amino-acid sequence which further differs from the amino-acid sequence of SEQ ID NO:1 by at least one additional amino-acid replacement selected from the group consisting of N42R, N114R, N115R, Q135R, M216Q, N237P, and T249R.

9. A composition according to claim 8, wherein the protease has an amino-acid sequence which differs from the amino-acid sequence of SEQ ID NO:1 by the amino-acid replacements Q12R, N42R and N114R.

* * * * *

UNITED STATES PATENT AND TRADEMARK OFFICE
CERTIFICATE OF CORRECTION

PATENT NO. : 5,880,080
DATED : March 9, 1999
INVENTOR(S) : Antoine AMORY, et al.

It is certified that error appears in the above-identified patent and that said Letters Patent is hereby corrected as shown below:

Column 18, line 66, after "amino acid sequence of" insert --SEQ--.

On the title page, in Other Publications:

Line 10, delete "gen" and insert --Gen.--.

Line 12, delete "Bold" and insert --Cold--.

Lines 16-17, delete "*Natt. Acaa. SCT.*" And insert --Nat. Acad. Sci.--.

Signed and Sealed this

Twenty-eighth Day of March, 2000

Attest:

Q. TODD DICKINSON

Attesting Officer

Commissioner of Patents and Trademarks